United States Patent

Ries et al.

[11] 4,058,000
[45] Nov. 15, 1977

[54] ULTRASONIC IMMERSION TYPE TESTING

[75] Inventors: Karl Ries, Mulheim; Kurt Hannoschöck, Sonsbeck; Günter Simoneit, Mulheim, all of Germany

[73] Assignee: Mannesmann Aktiengesellschaft, Dusseldorf, Germany

[21] Appl. No.: 770,587

[22] Filed: Feb. 22, 1977

[30] Foreign Application Priority Data

Feb. 20, 1976 Germany .............................. 2607485

[51] Int. Cl.² ............................................. G01N 29/04
[52] U.S. Cl. ..............................................; 73/644; 73/662
[58] Field of Search ...................... 73/71.5 US, 67.5 R, 73/67.8 R

[56] References Cited

U.S. PATENT DOCUMENTS

| 3,074,268 | 1/1963 | Rafferty et al. ................... 73/67.5 R |
| 3,913,386 | 10/1975 | Saglio ........................... 73/67.8 R X |

FOREIGN PATENT DOCUMENTS 175,300  2/1966  U.S.S.R. .......................... 73/71.5 US

Primary Examiner—James J. Gill
Attorney, Agent, or Firm—Ralf H. Siegemund

[57] ABSTRACT

The entrance angle of an ultrasonic beam into a test object results from refraction at the interface thereof with water. The physical orientation of the transducer directing a beam towards the object is maintained, but the refraction angle is varied through controlled adjustment of the water temperature.

2 Claims, 6 Drawing Figures

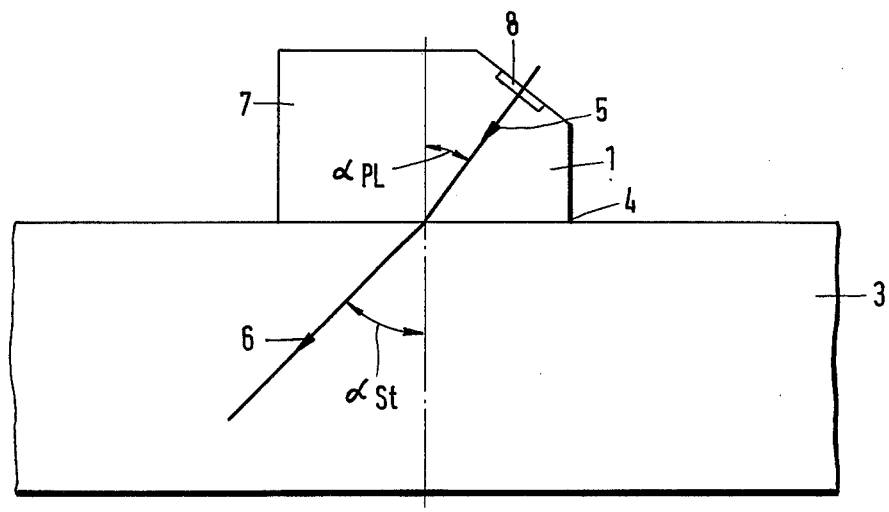
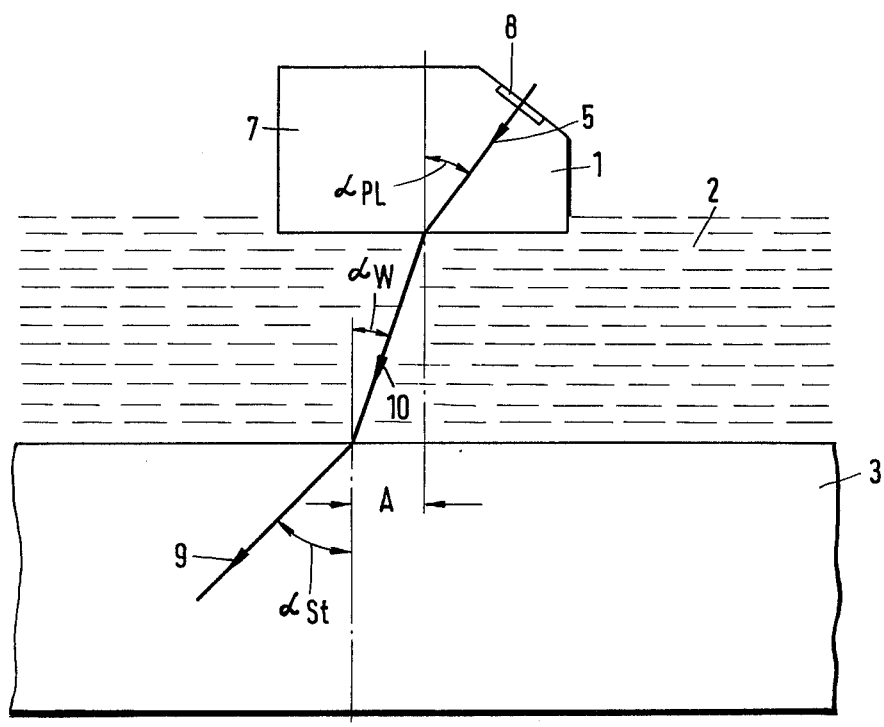

ULTRASONIC IMMERSION TYPE TESTING

BACKGROUND OF THE INVENTION

The present invention relates to improvements in a method of ultrasonic testing of objects such as pipes, strips, sheets, etc.

Ultrasonics is a well established technique for nondestructive testing of a variety of objects, particularly for inspecting the interior of the object for purposes of detecting any flaws and defects therein. One may distinguish here between two types of flaws or defects. One kind runs predominantly transversely to the surface of the test object, and one speaks here of transversal and of longitudinal flaws, depending upon the relation between the flaw and the predominant extension of the object. These flaws are usually detected through so-called transverse waves. The other type of defects or flaws extends predominantly parallel to a surface of the object and are usually detected by means of longitudinal waves.

The beam of ultrasonic transverse waves enters the test object usually at an angle between 33° and 90°. The most suitable angle used in each instance depends upon experience; different test objects and particularly differently contoured test objects have quite frequently their own and unique "best" entrance angle. For example, seamless pipes are tested with an entrance angle of the ultrasonic radiation beam in the range from 40° to 55°, using particularly the single transducer pulse echo method. Testing of longitudinally or spirally seam welded pipes is carried out by means of test heads being oriented to produce entrance angles of 45°, 60° and 70°. The inspection of pipes requires beams which, from the interior of the pipe impinge upon the inner wall surface at 74°.

The relation of the most suited entrance angle does not just depend on the best suited orientation as far as the expected flaws is concerned, but one must consider the conditions under which such waves are produced and reflect at the test object. In particular, side effects of the beam may produce erroneous indications.

For example, transducers directing beams at particular angles towards the test object, produce also edge effect or fringe radiation which reaches the test object at different angles, and the conditions for reflection and propagation differ from those of the desired test beam. The reception of such waves by a pickup detector may simulate nonexisting defects.

If the angle of incidence is very steep, one produces increasingly longitudinal waves in addition to transverse waves, which may also lead to incorrect readings. If the angle of incidence is very shallow, e.g., more than 70°, edge effect radiation may produce surface waves which are very sensitive in surface near regions, and produce incorrect detection reading accordingly. All these side effects limit the choice of the entrance angle of a test beam into the test object, which, in turn, means that such angles have to be particularly set up and critically maintained.

As stated above, cylindrical objects such as rounds, rods, pipes, etc., are tested primarily by means of transverse waves. The particular entrance angle for the transverse waves can be obtained in various ways, and involved here is particularly the test head and transducer construction as well as the mode of coupling the transducer to the test object.

With very few exceptions, all methods, modes of coupling, and test head constructions, provide transverse waves into the object indirectly, i.e., by means of refraction of a longitudinal wave, being directly produced by the transducer. As the longitudinal wave impinges upon the surface of the test object, the wave is refracted and a transverse wave propagates into the test object. The desired entrance angle for that transverse wave is the refraction angle of the incident beam.

Cylindrical objects are tested by means of transverse waves resulting from obliquely positioned transducers which radiate at a fixed angle of incidence towards the test object. These angle beam heads have a particular coupler medium in which the ultrasonic wave fronts are produced at a particular angle in relation to a coupler surface. These heads produce one particular refraction angle for the entrance beam as propagating into the test object from the interface thereof with the coupler surface. This physical relation between transducer or test head and the test object is indeed a fixed one and results in a definite entrance angle for the test beam. However, this particular angle has validity only for a particular test material. The coupler medium and the orientation of the oscillator are fixed parameters. Thus, if such a head is applied to a different test object (different material), the angle may no longer be valid.

Automated test stands in a production line have their own particular requirements, including particular consideration for the life of the equipment. Also, these requirements involve, for example, changes such as a replacement or exchange of test heads for purposes of changing the needed entrance angles. Accordingly, a variety of systems have been developed which permit pivoting of the angle beam heads for purposes of changing the angles of incidence. These holders are often constructed in accordance with the type, contour, etc., of the object to be tested, and they are quite unique with the test object concerning the needed adjustment angles. Also, angle beam heads with variable entrance angles have been developed.

Another point to be considered is that often fluid coupler media are interposed between the test heads and the test objects. The test head if of angle type construction, includes usually a wedge element as stated to establish a particular relation between the direction into which the transducer oscillator transmits it vibrations, and the coupler surface from which the beam emerges. If a fluid is interposed, that coupler surface interfaces with the fluid and not with the test object. Hence, there are two interfaces for a beam, one between the transducer coupler element and the coupler fluid, and a second one between that fluid and the test object. The ultrasonic waves are refracted on both surfaces, but these two refractions, in effect, cancel each other out, so that again only the relationships between the solid media remains determining for the entrance angle of the beam into the test object. In other words, the entrance angle of the beam into the test object remains unaffected by the presence or absence of the coupler fluid. Still in other words, the coupler fluid does not operate as a modifier for the entrance angle of the inspection beam. Thus, the change of that angle is a matter of position adjustment of the transducer. It is quite detrimental here that the resulting entrance angle is quite difficult to reproduce and is also to be determined to begin with.

DESCRIPTION OF THE INVENTION

It is an object of the present invention to improve methods of inspecting objects by means of ultrasonic waves for detecting defects and flaws therein, and wherein a coupler fluid is provided between the ultrasonic transducer and the test object, permitting in particular adjustment of the entrance angle of such a beam into the object in a manner that is independent from operating personnel.

In accordance with the preferred embodiment of the invention, it is suggested to control the temperature of the coupler fluid for adjusting the existing speed of sound thereof so that the effective index of refraction at the fluid-test object interface is varied towards the desired value, while the angle of incidence of the test beam remains unaffected or is maintained constant. Having adjusted the temperature, it must be kept constant.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

FIG. 1 illustrates somewhat schematically an ultrasonic transducer of the angle beam variety having a solid coupler medium and direct surface to surface contact thereof with a test object;

FIG. 2 illustrates a similar arrangement except that water gap is interposed as an additional coupler medium between the test object and the angle beam head;

Proceeding now to the detailed description of the drawings, FIG. 1 illustrates an ultrasonic test head 7 having a transducer 8 of which is only shown the active vibrating or oscillating element. The test head 7 is of the angle beam variety and is, therefor, additionally comprised of a body of Plexiglas. The body 1 has an oblique surface to which is attached or which includes the oscillator 8 and which defines the direction of transmission of a beam 5 of ultrasonic vibrations. The body 1 has a coupler interface 4 which that beam reaches at an angle $\alpha_{PL}$ and by means of which the test head is coupled to a surface of a test object 3, there may be a sheath of, e.g., liquid interposed to ensure intimate contact. As transducer 7 is coupled to test object 3, the beam 5 impinges upon the test object's surface and is refracted in the interface 4. The test object is presumed to be made of steel, i.e. it may be to a steel plate, bar or the like.

Figure 3:
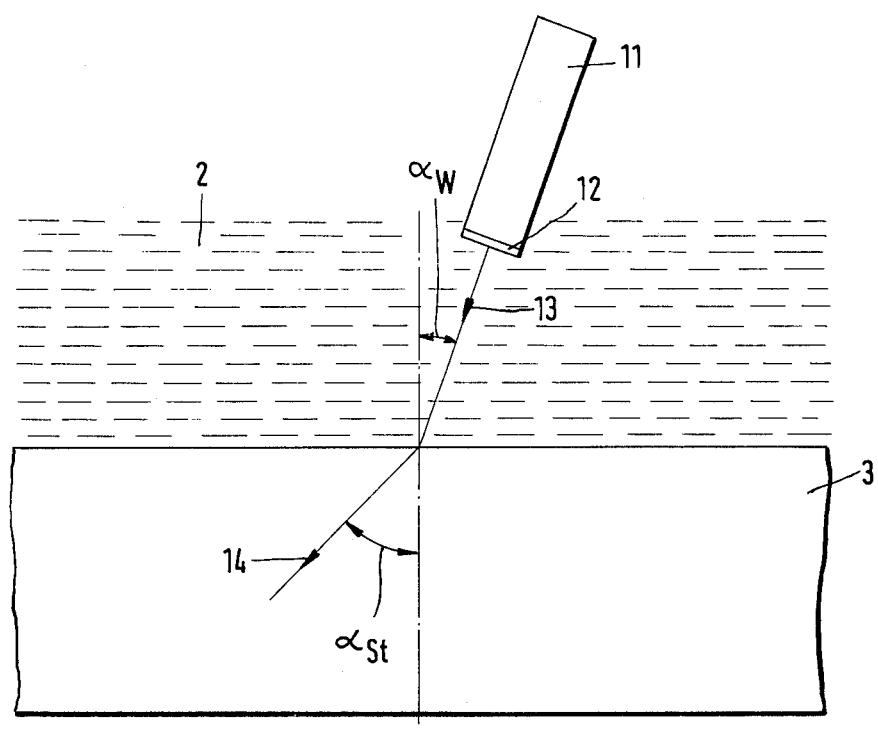
FIG. 3 illustrates an arrangement in principle for practicing the inventive method and using immersion type testing.

It may be assumed that vibrator or oscillator 8 produces the longitudinal ultrasonic wave 5, while a transverse wave 6 penetrates object 3 as the refracted beam. Since the velocities of the ultrasonic waves differ in the two media 1 and 3, refraction occurs at the interface 4; i.e. for a nonzero angle $\alpha_{PL}$ of incidence, the beam continues into medium 3 at an angle $\alpha_{ST}$, which is different from $\alpha_{PL}$. The speed of sound $C_1$ of a longitudinal wave in Plexiglas is $2.7 \cdot 10^3$ m/sec at 20° C and the speed of sound $C_3$ of a transverse wave in steel is $3.2 \times 10^3$ m/sec. Thus, the refraction angle $\alpha_{SL}$ is given by the relation of incident and refracted beams, $\sin \alpha_{ST} = \sin \alpha_{PL} \cdot C_3/C_1$. The example shows an angle of incidence $\alpha_{PL}$ of 37° so that the refraction angle will be equal to 45.3°. That angle is the entrance angle of the flaw probing beam 6.

Generally speaking, the speed of sound is dependent upon temperature. Hence, if the temperature changes in either medium, $\alpha_{ST}$ changes for constant $\alpha_{PL}$ (or viceversa). Specifically, entrance angle $\alpha_{ST}$ does not just depend on the temperature of the test medium, but also on the temperature of the coupler medium as it extends between vibrator 8 and test object 3. Please note that a variation in temperature of coupler medium 1 does not change the angle of incidence per se, because that angle is given exclusively by the geometry of the angle block 1.

Krautkramer found that a temperature change in the Plexiglas body 1 by ± 10° C from 20° C, causes the refraction angle $\alpha_{ST}$ to vary by ± 0.3°, if the angle of incidence of the test head is 45°. For angles of incidence, on account of test head construction, of 60°; 70°; 80°; the entrance and refraction angle $\alpha_{ST}$ changes respectively ± 0.5°; ± 0.8°; ± 1.5° from the respective normal value at 20° C for the Plexiglas body. In reality then that angle change is quite small and can be neglected in most instances.

Next, it will be shown that these angle beam heads exhibit the same behaviour as to temperature dependency irrespective of the type of coupling used, i.e. irrespective of the interpositioning of a coupler fluid between the bodies 1 and 3.

FIG. 2 illustrates a coupler fluid path or water gap 2 being interposed between test object 3 and angle beam head 7. If one again designates the partial angle of incidence by the non-zero angel $\alpha_{PL}$, then the wave now is refracted in the opposite direction as it passes into the water, because water has a lower speed of sound than Plexiglas.

The beam progresses through the water along the rather steep path 10, still as a longitudinal wave, but is refracted again away from the normal upon traversing the interface between water and steel. Please note that the entrance angle $\alpha_W$ of the beam into the water is the same as the angle of incidence $\alpha_W$ as the transversal wave 10 impinges upon medium 3. Moreover, the refraction angle $\alpha_{ST}$ at which the beam 9 proceeds into test object 3, is the same as in the case of FIG. 1. The reason, of course, is to be seen in that the angle $\alpha_W$ is given by the relation $\sin \alpha_W = \sin \alpha_{PL} \cdot C_3/C_2$ and $\alpha_{ST}$ follows from the relation $\sin \alpha_{ST} = \sin \alpha_W \cdot C_2/C_1 = \sin \alpha_P \cdot C_3/C_2 \cdot C_2/C_1$, wherein $C_2$ is the speed of sound in water. If for any reason $\alpha_W$ changes, for example, because of a change in water temperature, that change does not affect the entrance angle $\alpha_{ST}$. In other words, the interposition of a coupler medium such as water does not change the angle of refraction at the test object, and that angle is invariant to temperature changes of the medium 2. However, the point of entrance into the test object was shifted by the distance A, and that point will change when the temperature of the medium 2 changes.

The situation is different in FIG. 3. The FIG. 3 illustrates a regular test head 11 whose vibrating or oscillating element 12 is coupled directly to a liquid medium 2. The head 11 is mounted in a particular position so that the beam 13 as emanating directly from the vibrator 12 impinges upon the test object 3 at a particular angle $\alpha_W$. That angle results from the particular orientation of the vibrating and oscillating surface of element 12 as it is coupled to the liquid medium 2. It is not important whether or not the particular vibrating surface of the transducer in contact with the liquid does, in fact, pertain to the active element. Decisive is that the direction of wave as it leaves the transducer and enters the coupler fluid is determined by the orientation of the transducer as such, and by the angle of the transducer surface and of beam path as determined therewith to the surface of test object 3. This angle of orientation is the desired angle of incidence.

The coupler medium usually employed is water, but in cases one has used a mixture of water and ehtyl alcohol. The head 11 could be mounted so that the angle of incidence $\alpha_W$ is varied from 0° to 27.5° for obtaining all possible entrance angles $\alpha_{ST}$ in steel as material of the test object. This technique is also known as immersion type test. It will now be explained how the inventive method can be practiced without the need for such a wide range adjustability.

The test beam 13 is refracted at the interface water-test object in accordance with the relation $$\frac{\sin \alpha_W}{\sin \alpha_{ST}} = \frac{C2}{C3} \text{ wherein } \alpha_{ST}$$

is again the angle to the normal for the path 14 along which the transversal wave propagates into the steel. $C_2$ is the speed of sound of the longitudinal wave in water which is $1.48 \cdot 10^3$ m/sec for water at a temperature of 20° C. $C_3$ is again the speed of a transversal wave in steel being $3.2 \cdot 10^3$ m/sec. However, unlike the previous relationships, the angle $\alpha_W$ is not just the entrance angle for the beam into water, it is also the orientation angle of the transducer in relation to the normal direction on the test object's surface.

The speed of sound in water is quite extensively dependent upon temperature. As stated above, in the example of FIG. 2, the temperature dependency of the speed of the ultrasonic wave in water and the resulting change in refraction at interfaces is cancelled in the case of double refraction and parallel boundaries. In the example of FIG. 3, the temperature dependency of the refraction can be cancelled also by interposing, e.g., a wedge of Plexiglas or the like between the vibrator 12 and the water, so that a second interface is set up at which occurs a refraction which will cancel any temperature dependency of the angle of incidence.

Another way of eliminating the temperature dependency of $\alpha_{ST}$ has been through the use of additives to the water, e.g. alcohol. It was found that upon adding about 15 to 20% ethyl alcohol to water, the speed of sound will vary very little in the temperature range from 0° to 30° C. Another way of eliminating temperature dependency is to keep the temperature of the coupler fluid constant. This last aspect is important, as it is a necessary requisite for practicing the invention with advantage.

Figure 4:
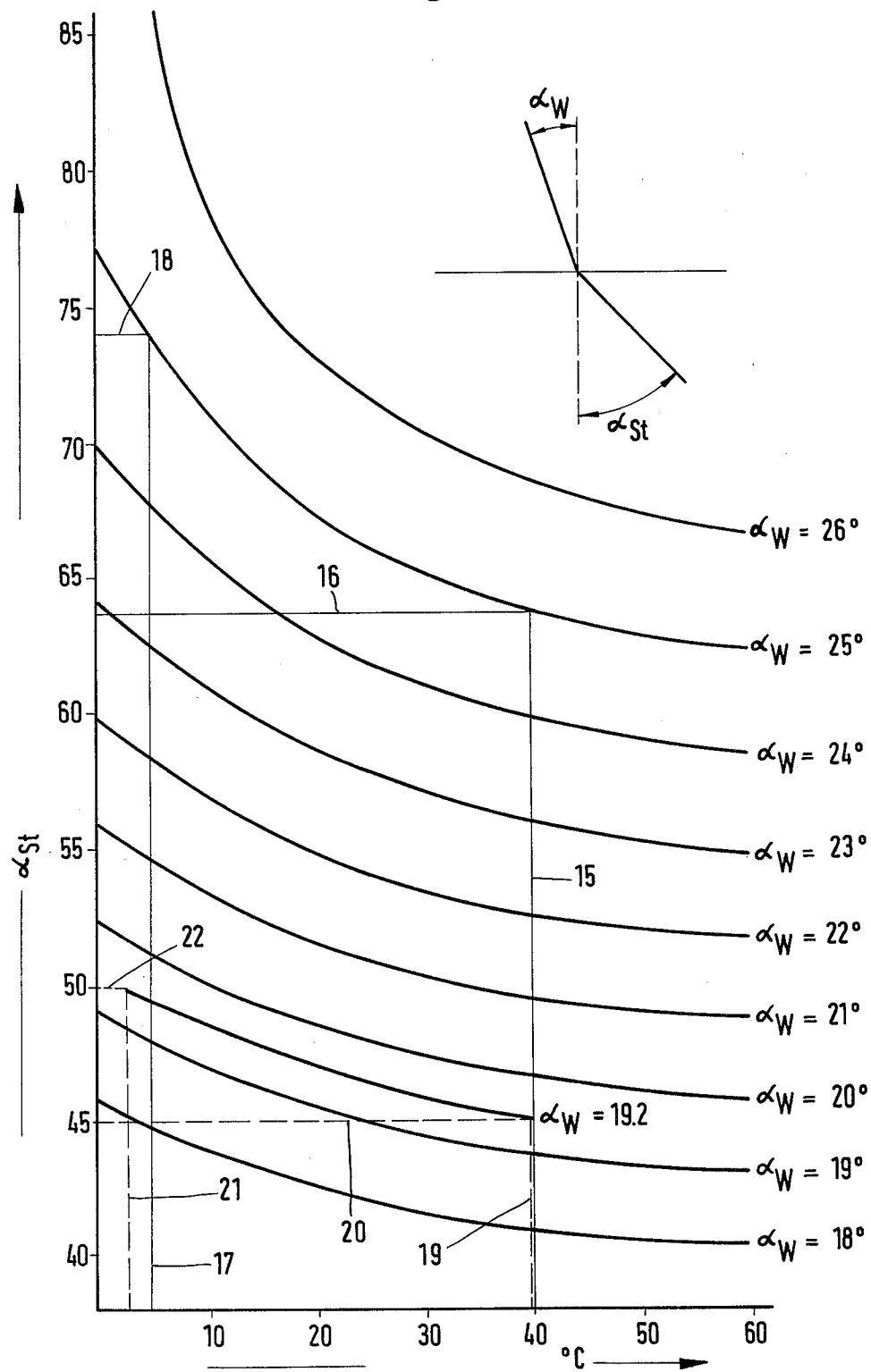
FIG. 4 is a graph showing the dependency of the entrance and refraction angle upon water temperature.

FIG. 4, taken in conjunction with FIG. 3, will now be used to explain the operation of the invention. FIG. 4 shows a refraction angle $\alpha_{ST}$ plotted against the temperature of water interfacing with steel into which the beam is transmitted; $\alpha_W$ is the angle of incidence and serves as the temperature for the group of calculated curves. The plot covers particularly the temperature range from 0° to 60°. The parameter range is from 18° to 26° angle of incidence.

One can readily see that the refraction angle $\alpha_{ST}$ changes quite significantly for temperatures and temperature changes below about 45° C, and for an angle of incidence of $\alpha_W$ 25° (see lines 15/16), the refraction angle is about 63.6°. When the temperature drops to 5° (line 17) the refraction angle rises to 75° (line 18). Consequently, for a fixed angle of, say, 25° adjusted position of transducer 11, one can adjust the refractor and entrance angle from 63.6° to 74° by changing the temperature from 40° C to 5° C, or to say it differently, an angular range from 63.6° to 74° for the entrance of the inspection beam is equivalent to a range of angle of incidence from a little under 73° to 25° but that latter range can be covered by keeping the angle of incidence constant at 25° and by changing the temperature of the coupler fluid-water.

The advantages of the inventive method are immenent. An adjusted range by a little over 2° for orientation adjustment of the test head 12 is equivalent to a temperature change by about 35°. Clearly, that latter change can be effected much more accurately than a two degree adjustment except under utilization of very expensive positioning equipment. Also, the temperature of the fluid medium 2, once adjusted, should be kept constant, but variations in temperature by a few degrees will affect the measurement very little. Also, readjustment of the temperature to the desired value through cooling or heating is a much simpler and more flexible mode of operation than, say, any realignment or reorientation of an adjustable transducer which has become misaligned for any reason.

Figure 5:
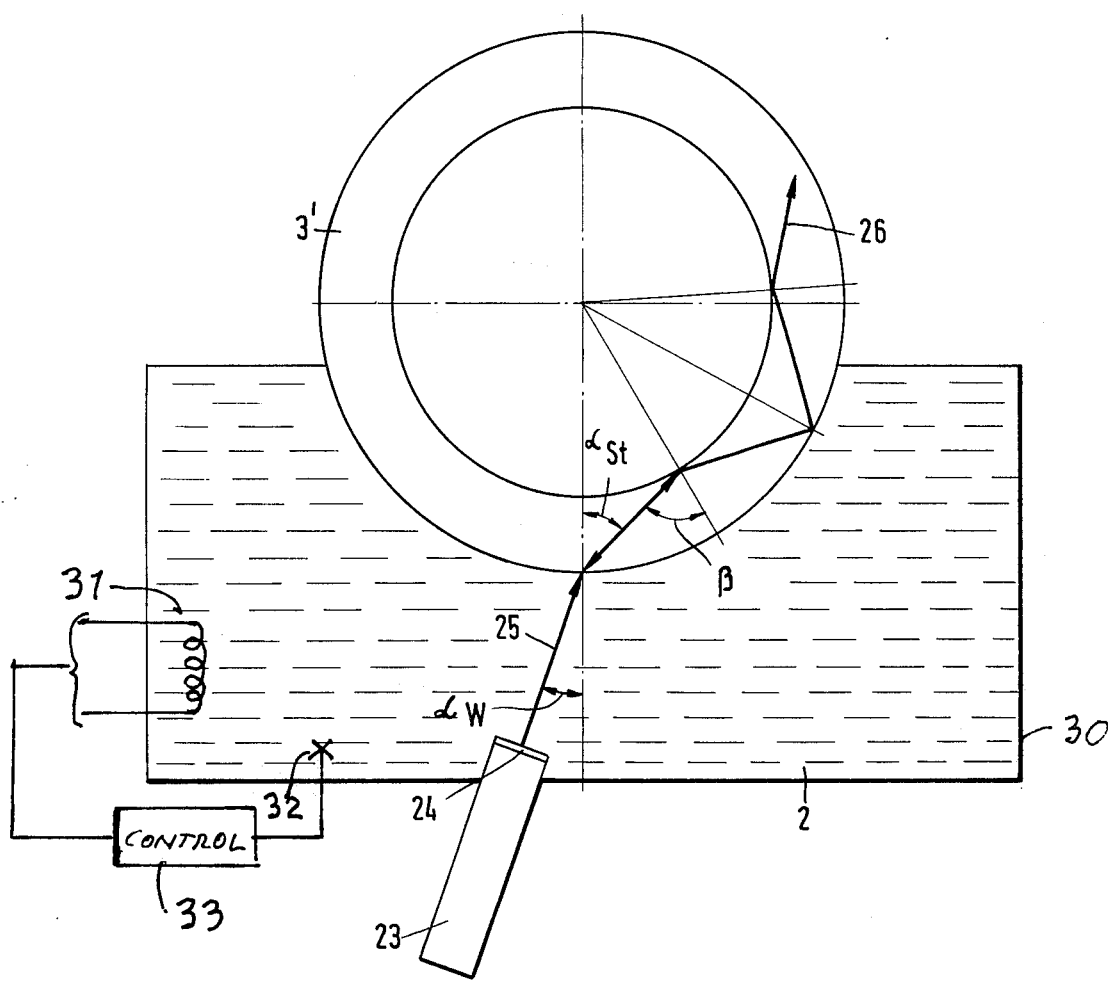
FIGS. 5 and 6 are schematic, cross-sectional views through different pipes, each being partially immersed in a coupler liquid and illustrating the path of a beam of ultrasonic energy.

FIG. 5 shows a first specific instance for practicing the invention. Water 2 is contained in a tank 30, and a pipe 3' is immersed partially in the water. The tank contains a transducer of the regular variety having a front end vibrator 24 from which emanates a beam 25 of longitudinal, ultrasonic waves. The beam impinges upon the pipe, e.g. at or near the lowest point of immersion and at an angle of, say 19.5°. This may be a fixed adjustment or even a fixed amount as far as the position of the head in its holder is concerned.

The pipe 3' is assumed to have 90 by 12 dimensions, and the water has been heated to a temperature of 40° C. The heater 31 denotes schematically that tank 30 is being heated, and thermo feeler 32 senses the temperature so that controller 33 will maintain the temperature constant.

In accordance with the plot of FIG. 4, this angle $\alpha_W$ of incidence produces a refraction angle $\alpha_{ST}$ of 45°, for the transversal wave, propagating into the pipe (lines 19/20). Due to the curvature of this particular pipe, the wave 26 impinges upon the inner wall at an angle $\beta$ of incidence of 74°. This angle is of great significance for locating flaws near that inner wall. This particular angle of 74° is, therefor, produced by providing for an entrance angle for the test beam 26 of 45°, and the latter results from the combination of the fixed head angle of 19.2°, and a temperature of 40° for the coupler fluid.

Figure 6:
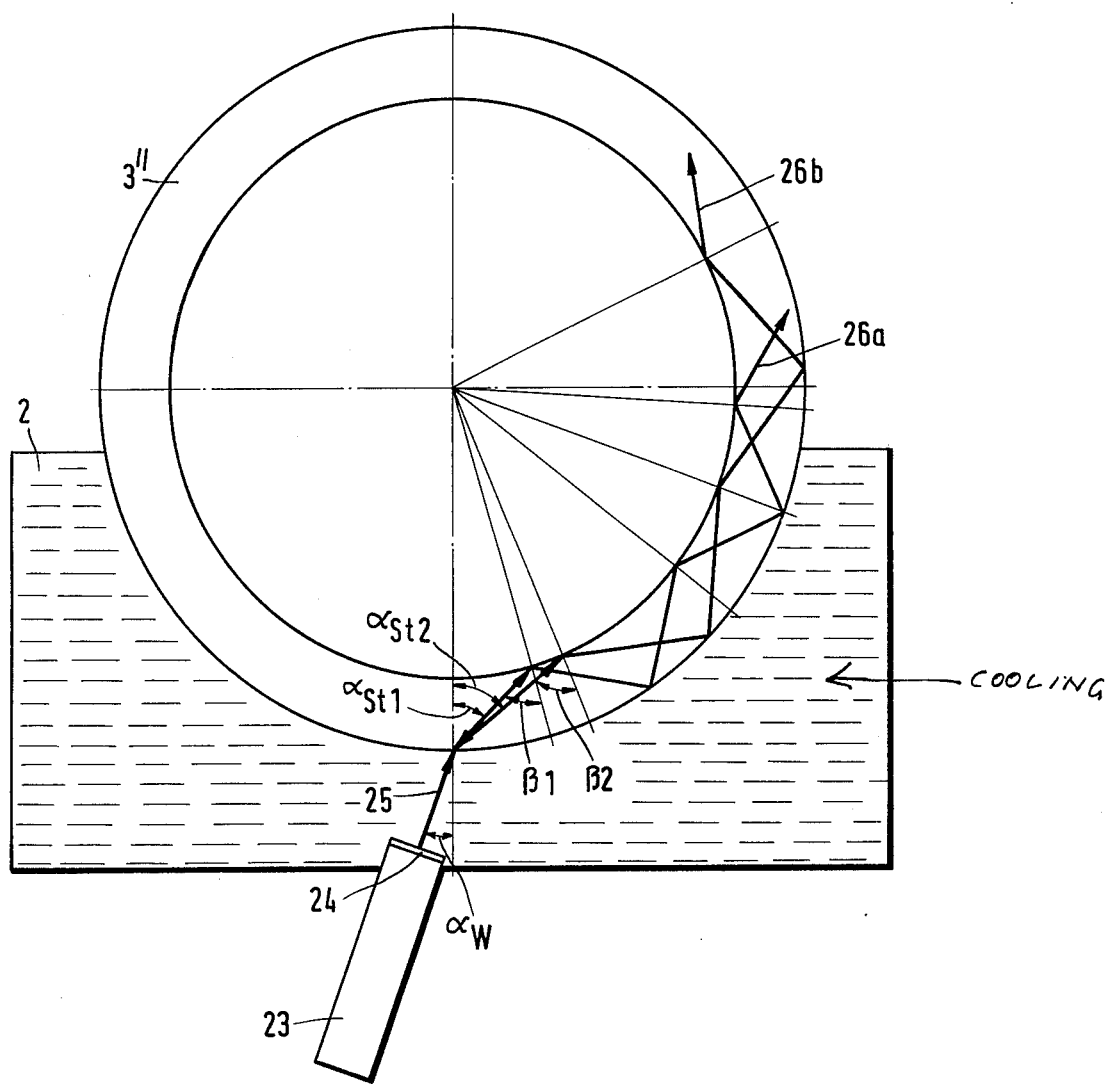

Now the same tank and equipment is used (FIG. 6) to test a much larger pipe 3" of the 120 by 12 variety. The angle of incidence is the same as transducer 23 has the same orientation. Accordingly, the refraction angle will be again 45°, if the water is still at 40°. The curvature of this pipe 3" is different and now the angle $\beta_1$ at the inner wall has dropped to 63°. In order to attain the desired angle of 74° ($\beta_2$), the refraction angle must be changed to about 50°, denoted as $\alpha_{ST2}$ in FIG. 1. In order to achieve this, the water temperature is dropped from 40° C to 2.5°, i.e., one changes the temperature, e.g. through in flow of cold water and continued, regulating cooling. The refraction angle now changes along the curve in the plot of FIG. 4, associated with the $\alpha_W = 19.2$ value, and 50° is reached when the water temperature has dropped to 2.5° C. This temperature change changes the path of the beam in the pipe material for a change in direction from 45° to 50° ($\alpha_{ST} \rightarrow \alpha_{ST}$), the angle of incidence upon the innerwall surface changes from $\beta_1$ to $\beta_2$, which is from 63° to 74°.

It can be seen that the invention permits employment of regular test heads with fixed orientation. A comparison of FIGS. 5 and 6 reveals that due to the different depth of immersion, the transducer has different distance from a vertical plane through the axis of the pipes. This, however, amounts merely to a lateral displacement of the transducer, or a lateral offset of the pipes. For more universal equipment, these test heads may be adjustable, say, into several fixed positions for a coarse adjustment and fine tuning is then carried out by temperature control. FIG. 4 readily reveals that for many given angles of incidence ($\alpha_W$), temperature control covers a more or less wide range of refraction angles. Thus, fixed adjustments to, say 25°, 23°, 21°, and 19°, of the test heads, will in actually permit covering an angle range for the refraction angle from about 40° to 75° in as fine steps as available through temperature control of the water. It was also found that readjustment in the form of changing temperature amounts to a faster equipment change than fine-tuning type orientation adjustment of the heads. The angles of refraction are also more accurately determinable.

The invention is not limited to the embodiments described above but all changes and modifications thereof not constituting departures from the spirit and scope of the invention are intended to be included.

We claim:

1. In a method of inspecting test objects for detecting defects by means of ultrasonics using the immersion test method, wherein a transducer directs a beam of ultrasonic waves towards the test object through water, the improvement comprising:

the step of adjusting the temperature of the water for a fixed orientation of said transducer relative to the test object, to change the refraction angle of the beam into the test object.

2. In a method as in claim 1, and including the step following the adjusting step, of maintaining the water temperature constant.

* * * * *